United States Patent
Wyrobnik et al.

(10) Patent No.: US 9,289,474 B2
(45) Date of Patent: *Mar. 22, 2016

(54) AGENT FOR USE IN THE CASE OF FRUCTOSE INTOLERANCE

(71) Applicants: Daniel Henry Wyrobnik, Frankfurt (DE); Isaac Harry Wyrobnik, Frankfurt (DE)

(72) Inventors: Daniel Henry Wyrobnik, Frankfurt (DE); Isaac Harry Wyrobnik, Frankfurt (DE)

(73) Assignee: VITACARE GMBH & CO. KG, Frankfurt (DE)

( * ) Notice: Subject to any disclaimer, the term of this patent is extended or adjusted under 35 U.S.C. 154(b) by 199 days.

This patent is subject to a terminal disclaimer.

(21) Appl. No.: 13/833,092

(22) Filed: Mar. 15, 2013

(65) Prior Publication Data

US 2013/0202695 A1    Aug. 8, 2013

Related U.S. Application Data

(63) Continuation-in-part of application No. 12/544,242, filed on Aug. 20, 2009, now Pat. No. 8,460,911, which is a continuation-in-part of application No. PCT/EP2008/001294, filed on Feb. 20, 2008.

(51) Int. Cl.
| | |
|---|---|
| *C12N 9/92* | (2006.01) |
| *A61K 38/52* | (2006.01) |
| *A61K 38/54* | (2006.01) |
| *A23L 1/305* | (2006.01) |
| *A23L 1/03* | (2006.01) |
| *A23L 1/30* | (2006.01) |
| *A61K 38/44* | (2006.01) |
| *A61K 9/48* | (2006.01) |

(52) U.S. Cl.
CPC .................. *A61K 38/52* (2013.01); *A23L 1/034* (2013.01); *A23L 1/30* (2013.01); *A23L 1/3053* (2013.01); *A61K 9/485* (2013.01); *A61K 38/44* (2013.01); *A61K 38/54* (2013.01); *C12Y 101/99011* (2013.01); *C12Y 302/0102* (2013.01); *C12Y 302/01026* (2013.01); *C12Y 503/01005* (2013.01)

(58) Field of Classification Search
None
See application file for complete search history.

(56) References Cited

U.S. PATENT DOCUMENTS

2003/0113310 A1 * 6/2003 Van Laere et al. ........... 424/94.5

OTHER PUBLICATIONS

IUBMB Enzyme Nomenclature "EC 5.3.1.5" definition.*
Bhosale et al., Microbiological Reviews, Jun. 1996, vol. 60, No. 2, p. 281-282 Only.*

* cited by examiner

*Primary Examiner* — Kade Ariani
(74) *Attorney, Agent, or Firm* — Daniel Feigelson; Fourth Dimension IP

(57) ABSTRACT

There is provided in accordance with embodiments of the invention a method of treating or reducing the effects in a subject of a condition selected from fructose intolerance and impaired fructose metabolism, the method comprising administering to a subject in need of such treatment or reduction an efficacious amount of a glucose isomerase, other than in combination with 5-D-fructose dehydrogenase. Other embodiments are also disclosed.

19 Claims, No Drawings

AGENT FOR USE IN THE CASE OF FRUCTOSE INTOLERANCE

This application is a continuation-in-part of U.S. Ser. No. 12/544,242, filed Aug. 20, 2009, which is a continuation-in-part of PCT/EP2008/001294, filed Feb. 20, 2008, which claims priority from DE 10 2007 008 664.6, filed Feb. 20, 2007. The priority and/or benefit of each of these applications, as appropriate, is claimed, and contents of these applications are incorporated herein by reference.

This patent application discloses an agent for use in the case of fructose intolerance, which contains a compound that effects the conversion of fructose to glucose. The term fructose intolerance is used in the context of this patent application to mean not only the medically defined fructose intolerance and fructose metabolism disorder (see below), but any form of impairment of health or well-being that occurs as a result of the intake of fructose or fructose containing foodstuffs, or due to the release of fructose in the digestive tract of humans or animals from other substances, such as sucrose.

In the context of this patent application, the terms "food" and "foodstuff" are used as synonyms. They mean to also include feed in the sense of animal feed.

Fructose is a ketohexose and is an important energy providing ingredient of food. It is present in numerous foodstuffs, as a component of di- and oligosaccharides, and/or as free fructose. Food such as fruit and fruit juices contains large amounts of fructose, but in particular also sucrose, which is cleaved to fructose and glucose in the body. In the following, the term 'fructose containing' is used to mean all substances and foodstuffs that either contain fructose as such or in a form from which fructose can be released in the digestive tract. The 'fructose content' of substances and foodstuffs refers to all the fructose in a fructose containing food or substance in whatever form it is contained in such a food or substance (free and also e.g. as part of sucrose).

In contrast to glucose, fructose is assimilated into the mucosa cells of the small intestine by eased carrier-mediated diffusion. The enzymatic degradation starts in the liver by the action of the adenosine triphosphate (ATP) dependent fructokinase, whereby fructose is converted to fructose-1-phosphate. In the liver and in the kidneys, fructose-1-phosphate is cleaved to glycerine aldehyde and dihydroxyacetone phosphate by aldolase B.

Three different types of fructose metabolism disorder are known in humans, namely hereditary fructose intolerance, intestinal fructose intolerance (sometimes also referred to as fructose non-absorption or fructose-malabsorption), and fructose-1,6-diphosphatase deficiency. In addition, there is fructosuria, which generally does not require treatment according to current scientific thinking.

Hereditary fructose intolerance (HFI) results from a deficiency of aldolase B, an enzyme that is present in the intestinal mucosa, the liver, lymphocytes and the kidneys. This enzyme usually breaks down fructose-1-phosphate to fructose-1,6-biphosphate via intermediate stages. If an aldolase B deficiency is present, an excess of fructose-1-phosphate occurs, leading to an inhibition of glycogen breakdown and of gluconeogenesis and, in turn, to severe hypoglycemia with outbreaks of sweating, tremor, vomiting and cramps after the intake of fructose. Acidosis, kidney damage and aminoaciduria can occur if this remains undetected. In infants, the risk ranges from hemorrhages to sudden infant death syndrome.

The symptoms of the widespread intestinal fructose intolerance are different, and its incidence is showing an increasing trend, especially in the western industrialized nations, it is caused by a disorder of fructose absorption resulting from the impairment of transport processes in the mucosa of the small intestine. Those affected suffer from unclear abdominal symptoms and, as a result of the bacterial breakdown of the carbohydrates passing into the colon, the production of intestinal gases is increased, The symptoms include, e.g. a feeling of bloating, flatulence, colic-like stomachache, watery diarrhea, and bowel sounds, This is often incorrectly diagnosed as irritable colon.

Fructose-1,6-diphosphatase deficiency involves a deficiency of this key enzyme in gluconeogenesis. This causes an increase in lactate levels in the blood after fructose exposure and fasting hypoglycemia, with lactacidosis, seizures, muscular hypotension, and coma. The development of fatty liver also leads to hepatomegaly.

Not all disorders of fructose metabolism necessarily lead to severe fructose in-tolerance. However, even in mild disorders of fructose metabolism, health impairments are often to be observed, which hitherto could only be influenced by a change of diet. Excessive consumption of fructose containing foodstuffs can also lead to health impairments.

The above-mentioned symptoms and complaints could only be avoided up to now by maintaining a fructose-, sucrose- and sorbitol-free diet. However, it is very difficult for those affected to keep to such a diet, since fructose is contained in all fruits and many vegetables, and is widely used as a sweetener by the foodstuffs industry. All foods that contain, e.g. sucrose (household sugar) also have to be avoided. Such a diet, which is indeed very strict in the case of hereditary fructose intolerance, is not only difficult to keep to, it is also extremely unfavorable from a nutritional physiological point of view, and considerably impairs the quality of life of those affected. Not only those affected, but also the specialist community, consisting of doctors, specialists, nutritional scientists, nutritional advisers, specialist journalists, etc., have assumed for decades that there is no alternative to maintaining the diet described above. Research focused on an alternative to this diet has remained unsuccessful to date. An agent that would make it possible to do without maintaining such a diet and would allow the intake of fructose containing food would thus satisfy an urgent need for the many people affected that has existed for decades. It would overcome a prejudice that has been established in the specialist world and among those affected and mean a very considerable improvement and a dramatic step forward in the therapeutic and nutritional options in fructose intolerance, since, apart from maintaining a diet, there has simply been no therapy available up to now. Such an agent would also put an end to the as yet unsuccessful efforts of the specialist world to enable those affected to eat normally and to consume fructose containing meals without suffering side effects. All of this would apply all the more to an agent that additionally had no negative effects on health.

There is thus provided, in accordance with an embodiment of the invention, a method of treating or reducing the effects in a subject of a condition selected from fructose intolerance and impaired fructose metabolism, the method comprising administering to a subject in need of such treatment or reduction an efficacious amount of a glucose isomerase, other than in combination with 5-D-fructose dehydrogenase. In some embodiments, the condition is intestinal fructose intolerance. In some embodiments, the glucose isomerase is administered prior to said subject's eating, concurrently with the subject's eating or after the subject's eating. In some embodiments, the glucose isomerase is administered within 15 minutes of the subject's eating. In some embodiments, the glucose isomerase is administered within 10 minutes of the subject's eating. In some embodiments, the glucose isomerase is administered within 5 minutes of the subject's eating. In some embodiments, the glucose isomerase is administered with a second enzyme which cleaves fructose from a sugar that is more complex than fructose. In some embodiments, the second enzyme is selected from the group consisting of invertase, maltase and combinations thereof. In some embodiments, the administration comprises oral administration.

There is also provided, in accordance with an embodiment of the invention, a mammalian ingestible composition of matter selected from a pharmaceutical composition and a dietary supplement, said composition of matter comprising a glucose isomerase, a second enzyme other than 5-D-fructose dehydrogenase, and a carrier or excipient that is acceptable for use in pharmaceutical compositions, dietary supplements or foodstuffs. In some embodiments, the composition of matter is in unit dosage form. In some embodiments, the composition of matter is in an orally administrable form. In some embodiments, the composition of matter is in a form selected from (a) the group consisting of a tablet, capsule, gel cap, pellet, granules and dragee, (b) the group consisting of a solution, a suspension and a gel, optionally which is a contained in a single-dose container and (c) powder form which is contained in a single-dose container. In some embodiments, the composition of matter is contained in a device operable to deliver a single dose or single doses of the composition, such as a syringe for use with children adapted to deliver a single dose orally. In some embodiments, the glucose isomerase is protected by a coating which is stable at pH below 4. In some embodiments, the glucose isomerase is protected by a coating which dissolves at a pH of 5.5 or higher. In some embodiments, the composition of matter is in unit dosage form and the coating protects the entire dosage unit. In some embodiments, the glucose isomerase is microencapsulated. In some embodiments, the glucose isomerase constitutes between 5 and 99.9% by weight of the composition of matter. In some embodiments, the unit dosage form contains between 0.01 and 100,000 units of glucose isomerase activity. In some embodiments, the composition of matter comprises a coating which is stable at a pH below 4. In some embodiments, the composition of matter comprises a coating which dissolves at a pH of 5.5 or higher. In some embodiments, the glucose isomerase is not contained in an inorganic-based sol-gel biocompatible matrix. In the context of this patent application, the term "inorganic-based sol-gel biocompatible matrix" includes a silica-based sol-gel biocompatible matrix. In some embodiments, the second enzyme is selected from the group consisting of invertase, maltase and combinations thereof.

There is also provided, in accordance with embodiments of the invention, a foodstuff which comprises glucose isomerase, at least some of the glucose isomerase being present in the foodstuff in a form in which the glucose isomerase will be available in active form after ingestion of the foodstuff; a second enzyme other than 5-D-fructose dehydrogenase, at least some of said second enzyme being present in said foodstuff in a form in which said second enzyme will be available in active form after ingestion of said foodstuff; and wherein, to the extent the foodstuff contains 5-fructose dehydrogenase, the 5-fructose dehydrogenase will not be available to act on fructose which is present in or released from the food pulp in the digestive tract after ingestion of the foodstuff. In this manner, the glucose isomerase and, when present, the second enzyme will be available to act on their respective substrates which are present in or released from the food pulp present in the digestive tract. "Food pulp" in the context of this patent application constitutes any food, including that ingested before, concomitantly with or after the ingestion of the glucose isomerase-containing foodstuff, as well as the glucose isomerase-containing foodstuff itself, that the active glucose isomerase and, when present, active second enzyme encounter in the digestive tract. In some embodiments, the foodstuff is selected from the group consisting of a cooked foodstuff, and a liquid foodstuff. In some embodiments, the glucose isomerase is not contained in an inorganic-based sol-gel biocompatible matrix. In some embodiments, the glucose isomerase is microencapsulated. In some embodiments, the foodstuff is substantially free of substances which are not approved for oral human ingestion. In some embodiments, the foodstuff is not a dough or a dough premix. In some embodiments, the foodstuff is not a baked foodstuff. In some embodiments, the foodstuff is not a bread.

There is also provided, in accordance with an embodiment of the invention, a process for preparing a glucose isomerase-containing foodstuff, the process comprising adding to a foodstuff glucose isomerase in a form in which at least some of the glucose isomerase will be available in active form after the foodstuff is ingested by a subject, whereby to obtain the glucose isomerase-containing foodstuff. In this manner, the glucose isomerase will be available to act on fructose which is present in or released from the food pulp present in the digestive tract.

There is also provided, in accordance with an embodiment of the invention, a kit comprising glucose isomerase and instructions explaining how to use the glucose isomerase to diagnose, treat, or reduce the effects of a condition selected from fructose intolerance and impaired fructose metabolism. In some embodiments the condition is intestinal fructose intolerance (sometimes also referred to as fructose non-absorption or fructose-malabsorbtion. In some embodiments the instructions instruct to administer the glucose isomerase prior to the subject's eating, concurrently with the subject's eating or after the subject's eating. In some embodiments, the glucose isomerase is administered within 15 minutes of the subject's eating. In some embodiments, the glucose isomerase is administered within 10 minutes of the subject's eating. In some embodiments, the glucose isomerase is administered within 5 minutes of the subject's eating. In some embodiments the instructions instruct to administer the glucose isomerase with a second enzyme which cleaves fructose from a sugar that is more complex than fructose. In some embodiments the second enzyme is selected from the group consisting of invertase, maltase and combinations thereof. In some embodiments the instructions instruct oral administration. In some embodiments the instructions instruct to administer the glucose isomerase other than in combination with a 5-D-fructose dehydrogenase.

There is also provided, in accordance with an embodiment of the invention, a foodstuff which comprises glucose isomerase, wherein said foodstuff is not a dough or a dough premix. In some embodiments, the foodstuff is in unit dosage form. In some embodiments, the foodstuff is in a form selected from (a) the group consisting of a tablet, capsule, gel cap, pellet and dragee, (b) the group consisting of a solution, a suspension and a gel, optionally which is contained in a single-dose container, or (c) powder which is contained in a single-dose container. In some embodiments, the composition of matter is contained in a device operable to deliver a single dose or single doses of the composition, such as a syringe for use with children adapted to deliver a single dose orally. In some embodiments, the foodstuff is not a baked foodstuff. In some embodiments, the foodstuff is not a bread. In some embodiments, at least some of the glucose isomerase is present in the foodstuff in a form in which the glucose isomerase will be available in active form after ingestion of the foodstuff. In this manner, the glucose isomerase will be available to act on fructose which is present in or released from the food pulp present in the digestive tract. In some embodiments, to the extent the foodstuff contains 5-fructose dehydrogenase, the 5-fructose dehydrogenase will not be available to act on fructose which is present in or released from the food pulp present in the digestive tract after ingestion of the foodstuff. In some embodiments, the foodstuff is selected from the group consisting of a cooked foodstuff, and a liquid foodstuff. In some embodiments, the glucose isomerase is not contained in an inorganic-based sol-gel biocompatible matrix. In some embodiments, the glucose isomerase is microencapsulated. In some embodiments, the foodstuff is substantially free of substances which are not approved for oral human ingestion. In some embodiments, the foodstuff contains a second enzyme other than 5-D-fructose dehydrogenase, at least some of said second enzyme being present in said foodstuff in a form in which said second enzyme will be available in active form after ingestion of said foodstuff. In some embodiments, the foodstuff is labeled as being advantageous for persons who suffer from fructose intolerance and/or a fructose metabolism disorder.

In some embodiments, the glucose isomerase is isolated from a natural source. In some embodiments, the glucose isomerase is isolated from a recombinant source.

In some embodiments, the foodstuff further comprises a second enzyme which is selected from the group consisting of invertase, maltase and combinations thereof.

There are provided, in some embodiments of the present invention, an effective agent that can be used not only in milder disorders of fructose metabolism, but also in hereditary and intestinal fructose intolerance and in fructose-1,6-diphosphatase deficiency, especially in order to enable the consumption of normally fructose containing foodstuffs even if fructose intolerance is present. Some embodiments of the invention make it possible for those affected by fructose intolerance to eat foodstuffs that they were not allowed to eat up to now, due to their fructose content. Some embodiments provide an agent that can reduce or prevent the occurrence of fructose intolerance symptoms after the intake of fructose.

In some embodiments, there is provided an agent that contains glucose isomerase, other than in combination with 5-fructose dehydrogenase.

In this patent application, a glucose isomerase is an enzyme that is able to convert fructose into glucose. This conversion can also be achieved by a xylose isomerase. Thus, in the context of this patent application, a xylose isomerase is also a glucose isomerase. A possible method for producing a xylose isomerase is described in Yamanaka, Biochimica et Biophysika Acta, issue 151 (3), 1968, 670-680, "Purification, Crystallization and Properties of the D-Xylose-Isomerase from Lactobacillus brevis" and in Yamanaka, Methods in Enzymology, issue 41, 1971, 466-471, "D-Xylose Isomerase from *Lactobacillus brevis*"; these documents are hereby incorporated by reference.

The agent according to embodiments of the present invention can bring about the conversion of the fructose in food or in food pulp into glucose. The fructose so converted is thus no longer available for the bacterial metabolism in the intestines characterized by fermentation, and the likelihood of an excess of fructose-1-phosphate occurring in the liver or elsewhere is reduced. This can also prevent an increase in lactate levels in the blood.

There is provided in accordance with some embodiments an agent that reduces the bioavailability of fructose in the human or animal body with the help of glucose isomerase.

There is also provided in accordance with some embodiments an agent that, with the help of glucose isomerase, reduces the amount of fructose available to the human or animal body or to intestinal bacteria colonizing therein.

There is also provided in accordance with some embodiments an agent for use in the case of fructose intolerance, which contains glucose isomerase.

There is also provided in accordance with some embodiments the use of glucose isomerase in the case of fructose intolerance.

There is also provided in accordance with some embodiments the use of glucose isomerase for the production of a product for the use in the case of fructose intolerance.

Glucose isomerase, which belongs to the group of isomerases, is an enzyme that has the property of converting D-fructose into D-glucose and vice versa. Here, an equilibrium of approximately 50% glucose and 50% fructose is established, depending on ambient temperature. Whereas fructose is only absorbed slowly from the small intestine, glucose is a sugar that is easily digested and rapidly absorbed.

Thus, without wishing to be bound by theory, it is believed that some embodiments of the invention take advantage of the phenomenon of ingested fructose being converted into glucose in vivo by glucose isomerase that is consumed simultaneously or at least shortly before or thereafter. The glucose isomerase then attempts to achieve the above-mentioned equilibrium by converting fructose to glucose. However, glucose is absorbed very rapidly, so that the equilibrium cannot be achieved. Theoretically, the glucose isomerase may continue to convert fructose still available in the food pulp into glucose until no further fructose is left. The dose of glucose isomerase may be selected in such a way that, even if larger amounts of fructose are consumed, the reaction can take place quickly enough that substantially no fructose is absorbed or that the amount of fructose absorbed in the meantime is too small to cause the known gastrointestinal complaints in the case of mild fructose metabolism disorders and intestinal fructose intolerance and the known systemic complaints in the case of hereditary fructose intolerance and fructose-1,6-diphosphate deficiency.

As disclosed in co-pending application Ser. No. 12/093, 822, the enzyme 5-D-fructose dehydrogenase (syn. fructose 5-dehydrogenase) can bring about the conversion of the fructose in food to 5-keto-D-fructose by dehydrogenation. Thus, the fructose is changed in such a manner that it is no longer available to the metabolism of the human or animal body. A 5-D-fructose dehydrogenase in this sense is an enzyme that can bring about the dehydrogenation of fructose to 5-keto-D-fructose. Particularly favorable effects can therefore be achieved if glucose isomerase and 5-D-fructose dehydrogenase are used in combination. A possible method for the production of a 5-D-fructose dehydrogenase is, for example, described in Ameyama et al., Journal of Bacteriology 1981, 814-823, "D-Fructose Dehydrogenase of Gluconobacter industrius: Purification, Characterization and Application of Enzymatic Microdetermination of D-Fructose", the content of which is incorporated herein by reference.

Thus, disclosed in co-pending application Ser. No. 12/093, 822 is an agent that, beside glucose isomerase, additionally contains 5-D-fructose dehydrogenase. Such a combination agent can also be used in the form of two separate dose units, e.g. two separate tablets, one of which contains glucose isomerase and the other 5-D-fructose dehydrogenase.

In accordance with embodiments of the present invention, a glucose isomerase can be used to reduce the fructose content in a foodstuff. As disclosed in co-pending application Ser. No.

12/093,822, a glucose isomerase can be used in combination with 5-D-fructose dehydrogenase to reduce the fructose content of a foodstuff.

Foodstuffs in the sense of the present application also comprise, among other things, foodstuffs for particular nutritional uses, foods for special medical purposes, medical foods, food supplements, dietary supplements, dietetic food supplements, health foods, nutraceuticals, and food additives.

In some embodiments, the foodstuff may be labeled as being advantageous for persons who suffer from fructose intolerance and/or a fructose metabolism disorder. Such labeling (or, for that matter, any advertising material such as a product website) need not necessarily use the exact words "advantageous for persons who suffer from fructose intolerance and/or a fructose metabolism disorder"; the labeling (or advertising material such as a product website) may have words to similar effect. For example, the labeling (or advertising material such as a product website) may state that the foodstuff is suitable for sufferers of fructose intolerance (and may name the type of fructose intolerance); or that the foodstuff is low in fructose content or has a reduced fructose content, or is low in effective fructose content, i.e. the amount of fructose present as free fructose and fructose which can be cleaved from other molecules; or that the foodstuff contains glucose isomerase (and may indicate that the glucose isomerase is in active form); or that the foodstuff contains enzyme(s) that reduce the fructose content (and may indicate that the enzyme(s) lower the fructose content after consumption of the foodstuff); or the labeling may be a symbol of approval from an organization for fructose intolerance sufferers; or the labeling may provide instructions for use of the foodstuff as part of a regimen for treating fructose intolerance or mitigating the effects or symptoms of fructose intolerance; and the like. While it is contemplated that, in general, it is the packaging in which the foodstuff is packaged that will bear the labeling, it will be appreciated that this need not be the case, and that, for example, the foodstuff itself may bear such labeling, or that the foodstuff may be displayed in a place where such labeling is also displayed, even if not on the packaging. The labeling need not necessarily use the exact words "for treatment of fructose intolerance". The labeling or advertising material such as a product website may have words to similar effect, such as "for conversion of fructose to glucose" or "for conversion of excess fructose to glucose" or "for conversion of fructose to glucose in the small intestine". Furthermore, there is provided in accordance with an embodiment of the invention a method for inducing a person to use glucose isomerase to convert fructose to glucose in vivo, comprising providing a product containing glucose isomerase, advertising or causing to be advertised (for example on a web site, in an internet forum, or on a printed medium) that the glucose isomerase may be used to convert fructose to glucose, and supplying the product to the person. In some embodiments the product is supplied directly to the person, for example via ordering from a web site. In some embodiments the product is supplied indirectly to the person, for example via a wholesaler, a retailer or other third party.

Embodiments of the present invention facilitate the transformation of fructose in a foodstuff into a form that avoids the problems that accompany fructose intolerance. Thus, embodiments of the present invention also make it possible for people affected by fructose intolerance to consume such foodstuffs, which had to be avoided up to now because of their fructose content.

In accordance with embodiments of the present invention, glucose isomerase is further mentioned for use in medicine, for example as a pharmaceutical composition. Accordingly, in accordance with embodiments of the invention there is provided a product which contains or consists of glucose isomerase along with one or more other active ingredients, for use in a medical method, in particular in a method for the therapeutic treatment of the human or animal body. In this patent application, a pharmaceutical composition is a product, in particular a substance or a substance mixture, for use in a method for surgical or therapeutic treatment of the human or animal body or in diagnostic methods that are performed on the human or animal body. Thus, in this application, pharmaceutical compositions are also products, in particular substances or substance mixtures, that are intended or suitable for curing, alleviating, preventing or determining fructose intolerance.

In accordance with embodiments of the present invention, a foodstuff is provided which contains glucose isomerase in a form in which at least some of the glucose isomerase will exert its activity after ingestion of the foodstuff. In accordance with some embodiments, a foodstuff is provided that contains glucose isomerase in an amount which is sufficient to convert fructose into glucose after ingestion of the foodstuff. In some embodiments, such a foodstuff may be produced using a method for treating a foodstuff in which the foodstuff is placed in contact with a glucose isomerase under such conditions under which the glucose isomerase can convert fructose to glucose, provide that at least some of the glucose isomerase is incorporated into the foodstuff in a matter that it will exert activity after ingestion of the foodstuff. In contrast to otherwise untreated foodstuffs, such a foodstuff will effectively have a reduced fructose content after ingestion, and may have a reduced fructose content before ingestion as well, and therefore is suitable to be consumed by persons suffering from fructose intolerance. Thus in some embodiments, a foodstuff can be prepared by a method in which a glucose isomerase is added to the foodstuff in a manner in which the action of at least some of the glucose isomerase only starts after the intake of the foodstuff. Such a foodstuff that contains glucose isomerase has the same taste as an untreated foodstuff and is suitable to be consumed by persons suffering from fructose intolerance, due to the reduced fructose content which is established after eating.

In some embodiments, a medical device is provided that contains glucose isomerase. Thus in accordance with some embodiments there is provided a medical device which consists of a glucose isomerase or contains a glucose isomerase along with one or more other active ingredients. In this application a "medical device" means any instrument, apparatus, appliance, material or other article, whether used alone or in combination, including the software necessary for its proper application intended by the manufacturer to be used for human beings for the purpose of:
 diagnosis, prevention, monitoring, treatment or alleviation of disease,
 diagnosis, monitoring, treatment, alleviation of or compensation for an injury or handicap,
 investigation, replacement or modification of the anatomy or of a physiological process,
 control of conception,
and which does not achieve its principal intended action in or on the human body by pharmacological, immunological or metabolic means, but which may be assisted in its function by such means;

Any instrument, apparatus, appliance, material or other article that does not achieve its intended action in or on the human body is not a medical device in the context of this patent application.

In the following, embodiments of the invention will be described further in various aspects. If the term agent is used below, this also stands for a foodstuff, a medical device or a pharmaceutical composition.

Glucose isomerase is a compound that has been known for more than 40 years and has only been used for starch saccharification to date. In the industry, it is used for the conversion of glucose into fructose as well as for the conversion of fructose into glucose.

The agents in accordance with embodiments of the present invention can be taken orally before meals, with meals or immediately after meals, so that they can exert their converting effect on fructose in the food pulp. Preferably, the agents are taken just before meals, during meals or immediately after meals. The agents may contain the enzyme without further additives. However, in some embodiments the agents further contain additives that are pharmaceutically acceptable and/or acceptable for foodstuffs, such as extenders, binders, stabilizers, preservatives, flavorings, etc. Such additives are commonly used and well known for the production of pharmaceutical compositions, medical devices, foodstuffs, foodstuffs for particular nutritional uses, foods for special medical purposes, medical foods, food supplements, dietary supplements, dietetic food supplements, health foods, nutraceuticals, and food additives and specialists in this field know which additives in which amounts are suitable for particular presentation forms. In some embodiments, the agents contain as additives dicalcium phosphate, lactose, modified starch, microcrystalline cellulose, maltodextrin and/or fibersol.

In accordance with some embodiments, the agents can be added to a foodstuff before eating. They can even be added to the foodstuff at the production stage, with the aim of developing their effect only after consuming the foodstuff. This could possibly be achieved by microencapsulation, for example. In this way, the useable fructose content of the foodstuff would be reduced in a particularly advantageous way, without negatively affecting its taste. Therefore, in some embodiments of the invention there are provided preparations containing glucose isomerase that do not release at least some of this enzyme until it reaches the digestive tract of a human or animal, or let the enzyme become active in another way, especially in the stomach or small intestine. Therefore, in accordance with embodiments of the invention, glucose isomerase could be used for example in the production of sweets, fruit preparations (e.g. apple sauce), jam, honey, chocolate and chocolate products, bakery products (e.g. biscuits and cakes), breads, pastas, vegetable dishes, potato dishes, ice cream, cereals, dairy products (e.g. fruit yogurt and pudding), fructose containing beverages, fructose containing sauces (e.g. tomato ketchup) and fructose containing sweeteners. For dishes that are boiled or baked, the agents could, e.g. be mixed into or sprinkled onto them after cooling.

Since fructose is widely used as a sweetener in foodstuffs that are especially produced for diabetics, the addition of the agents in accordance with embodiments of the present invention to diabetic food before eating or the addition of the agents during the production of diabetic food is especially advantageous, to allow diabetics who suffer from fructose intolerance to eat diabetic food, such as the above mentioned foodstuffs in their respective form as diabetic foods.

The agents can also be added to a foodstuff to exert their effect on fructose originating from a different foodstuff. An example of this would be the addition of the agents to a spread so that the reduction of the utilizable fructose contained in the bread upon which the spread is spread occurs after ingestion of the bread, without impairing the taste of the bread. Another example would be mixed spices.

In some embodiments, the agents also contain other active ingredients.

For use in accordance with embodiments of the invention, the glucose isomerase may be formulated in any form which is suitable for the intended route of administration. For oral administration, the agents may be formulated in the form of capsules (coated or non-coated), tablets (coated or non-coated), capsules containing coated or non-coated pellets, granules, or micro- or mini-tablets, tablets pressed from coated or non-coated pellets, dragees, or micro- or mini-tablets, gel caps or, in liquid form, as a solution, drops, suspension or gel. The formulation of the agent in accordacne with embodiments of the present invention as a powder is particularly suitable for an admixture to a foodstuff. The powder may be sprinkled onto a meal or it may be mixed into a pulp or a beverage. It is particularly suitable if the agent offered as bulk powder is packed in single dosage amounts, such as in single bags or capsules, or if it is provided in a dosing apparatus. It is especially preferable if the agent is formulated as a powder or as granules in capsules or as a tablet that are administered orally.

For oral administration, the glucose isomerase may be mixed with acceptable excipients and/or carriers. The term "acceptable carrier" relates to either a carrier for pharmaceutical use or for use in a foodstuff such as a dietary supplement which directs the active ingredient to its target site and which does not have negative effects for the recipient, human or animal. However, the exact form of the carrier is not decisive.

The total amount of the carrier and/or excipients of an agent containing glucose isomerase is preferably between 5 and 99.9% by weight, more preferably between 10 and 95% by weight and even more preferably between 25 and 90% by weight of the composition.

Suitable excipients and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethyl cellulose, corn starch, modified starch, fibersol, gelatine, hydroxypropylmethyl cellulose and the like (including mixtures thereof). Preferable carriers include calcium carbonate, magnesium stearate, maltodextrin, dicalcium phosphate, modified starch, microcrystalline cellulose, fibersol, gelatine, hydroxypropylmethyl cellulose and mixtures thereof.

The various ingredients and the excipient and/or carrier are mixed and formed into the desired form using common methods. The presentation form which is intended for oral administration, such as a tablet or capsule, may be coated with a coating that is resistant to low pH values. This makes it possible for the enzyme to be released only when they reach the small intestine. Also a coating may be used which is not resistant against low pH values but which provides delayed release of the respective enzyme at low pH values. It is also possible to prepare the agent in accordance with embodiments of the present invention as coated (see above) pellets, granules, or micro- or mini-tablets which can be filled into non-coated capsules or which can be pressed into non-coated tablets. Suitable coatings are, for example, cellulose acetate phthalate, cellulose derivatives, shellac, polyvinylpyrrolidone derivatives, acrylic acid, polyacrylic acid derivatives and polymethyl methacrylate (PMMA), such as Eudragit® (from Rohm GmbH, Darmstadt), e.g. Eudragit® FS30D (releases the active constituent or constituents starting at a pH of around 6.8) and/or Eudragit® L30D-55 (releases the active constituent or constituents starting at a pH of around 5.5). If it is desired to release the enzyme(s) already at a lower pH value, this may be achieved e.g. by the addition of sodium hydroxide solution to the coating agent Eudragit® L30D-55, because in this case carboxyl groups of the methacrylate would be neutralised. Therefore, this coating will be dissolved, for example, already at a pH value of 4.0 provided that 5% of the carboxyl groups are neutralised. The addition of about 100 g of 4% sodium hydroxide solution to 1 kg of Eudragit® L30D-55 would result in a neutralisation of about 6% of the carboxyl groups. Further details about formulation methods and administration methods can be found in the 21st edition of "Remington: The Science & Practice of Pharmacy", published 2005 by Lippincott, Williams & Wilkins, Baltimore, USA, in the Encyclopedia of Pharmaceutical Technology (Editor James Swarbrick) and in Prof. Bauer "Lehrbuch der Pharmazeutischen Technologie", 18th edition, published 2006 by Wissenschaftliche Verlagsgesellschaft (ISBN 3804-72222-9). The contents of these documents are incorporated herein by reference.

Other suitable pharmaceutically or dietarily acceptable carriers or excipients include water, mineral oil, ethylene glycol, propylene glycol, lanolin, glyceryl stearate, sorbitan stearate, isopropyl myristate, isopropyl palmitate, acetone, glycerine, phosphatidylcholine, sodium cholate and ethanol, but are not limited thereto.

The compositions for use in accordance with embodiments of the present invention may also comprise at least one coemulsifying compound, such as oxyethylenated sorbitan monostearate, fatty alcohols such as stearyl alcohol or cetyl alcohol, or esters of fatty acids and polyols, such as glyceryl stearate, but not limited thereto.

Preferably, the agents to be used in accordance with embodiments of the present invention are provided in a stabilized form. Generally, stabilization methods and procedures which may be used include any and all methods for the stabilization of chemical or biological material which are known in the art, comprising e.g. the addition of chemical agents, methods which are based on temperature modulation; methods which are based on irradiation or combinations thereof. Chemical agents that may be used according to the present invention include, among others, preservatives, acids, bases, salts, antioxidants, viscosity enhancers, emulsifying agents, gelatinizers, and mixtures thereof.

Conventionally, the industrial production of enzymes is performed in a technical fermentation way using suitable microorganisms (bacteria, moulds, yeasts). The strains are recovered from natural ecosystems according to a special screening protocol, isolated as pure cultures as well as improved in their properties with respect to the enzyme spectrum and biosynthesis performance (volume/time yield). The enzymes can also be produced using methods to be developed in the future.

Glucose isomerase is commercially available (e.g. Novozymes A/S, Denmark and Danisco, Denmark) and is usually prepared in a microbiological way with the help of the microorganism Streptomyces murinus. However, practice of embodiments of the invention is not limited to utilizing enzymes that are commercially available at the moment, but generally relates to enzymes that can bring about the conversion of fructose, specifically or non-specifically, to glucose. The enzymes may also be prepared with the help of other microorganisms, such as fungi, in sufficient amounts and the required purities, also by the use of genetic engineering methods which are common today. If it is desired e.g. to produce the enzymes with other microorganisms, the genetic information of a microorganism which has been found initially by extensive screening and which has also been proven as a suitable source of the enzyme with the desired properties can be transferred to a microorganism which is normally used for the production of enzymes. Also the modification of the enzyme and the production of the enzyme by means of methods which are presently known or may be developed in the future in the area of industrial enzyme development and enzyme production, such as genetic engineering, is possible. The use and the manner of performing all these methods for developing and producing the enzyme with the desired purities and activities and with the desired properties, in particular with respect to the stability of the enzyme at various pH values, regarding the optimum of the pH value, the stability at various temperatures and temperature optimum, are well known to a person skilled in the art. The explanations in chapter 2 (page 82 to page 130) of the textbook "Lebensmittel-Biotechnologie and Ernahrung" of Heinz Ruttloff, Jürgen Proll and Andreas Leuchtenberger, published by Springer Verlag 1997 (ISBN 3-540-61135-5) describe these methods in detail. These methods are also described in "Advances in Fungal Biotechnology for Industry, Agriculture, and Medicine" by Jan S. Tkacz, Lene Langeand try, Agriculture, and Medicine" by Jan S. Tkacz, Lene Langeand (published in 2004, ISBN 0-306-47866-8), in "Enzymes in Industry: Production and Applications" by Wolfgang Aehle (Editor), published in 2004, ISBN 3527295925 and in "Microbial Enzymes and Biotransformations" by Jose-Luis Barredo (Humana Press 2005, ISBN 1588292533). These documents are herewith incorporated into the patent application by reference. All this also applies to the enzymes mentioned below that can optionally be added to the agent according to the present invention.

In this patent application, the activity of glucose isomerase is defined in units, whereby one unit is the amount of glucose isomerase that converts 1 g of fructose to glucose in 5 minutes at a pH of 7.5 and a temperature of 37° C. from an initial 10% solution of fructose by weight (i.e. 10 g fructose in 90 g water).

At an enzyme activity determined according to this definition, an agent in accordance with embodiments of the present invention should contain glucose isomerase in an amount or activity of 0.01 to 100,000 GIU (=glucose isomerase units), preferably 0.05 to 10,000 GIU and particularly preferably 0.1 to 1,000 GIU per dose unit.

The wide range of the above mentioned dosages may be explained by the fact that the agent may be used in connection with very different types of fructose intolerance, namely in hereditary fructose intolerance, intestinal fructose intolerance, and fructose-1,6-diphosphatase deficiency, in their range of different severities, and also in milder fructose metabolism disorders. Furthermore, the different dosages also result from the fact that strongly varying amounts of fructose are administered to the body, depending on the respective food. The enzyme should be used in a sufficient quantity so that it develops a sufficiently high enzyme activity, in other words sufficient glucose isomerase to convert an amount of fructose consumed in a normal meal (e.g. 10-50 g)—in free or bound form—into glucose.

The agent, in accordance with embodiments of the present invention, may comprise one or more additional enzymes, such as invertase (syn. beta-fructofuranosidase or beta-fructosidase), lactase (syn. beta-galactosidase), maltase (syn. alpha-glucosidase), alpha-amylase, beta-amylase, glucoamylase, pullulanase, isoamylase, amyloglucosidase, cyclomaltodextrin glucantransferase (CGTase). These enzymes have the property of releasing fructose and/or glucose from fructose and/or glucose containing substances and foodstuffs—alone or in combination with one or more of these enzymes—, whereby the enzymes pullulanase and isoamylase also increase the efficiency of glucoamylase and beta-amylase. All these enzymes are commercially available (e.g. BioCat Inc., Troy, USA or Novozymes A/S, Denmark or Amano Enzymes Inc., Japan or Sigma-Aldrich) and, up to now, have not been used in combination with glucose isomerase in the medical/pharmaceutical field, in particular not in the case of fructose intolerance. Examples for agents in accordance with embodiments of the present invention include: Glucose isomerase in combination with invertase, or Glucose isomerase in combination with maltase, or Glucose isomerase in combination with invertase and maltase.

For example, said invertase can release fructose from e.g. sucrose.

By the addition of one or more of these enzymes to the agent, the endogenic release of fructose from fructose-containing substances or foodstuffs, in particular from sucrose, may also be promoted and accelerated, so that the conversion of fructose into glucose may occur earlier. Therefore, the addition of one or more of these enzymes to the agent may have the benefit of reducing the required amount of glucose isomerase.

The activity of invertase is measured in Sumner units (SU, assay available e.g. from Bio-Cat Inc., Troy, Va., USA). An SU is defined as the amount of the enzyme which converts 1 mg of sucrose into glucose and fructose under standard test conditions within 5 minutes at 20° C. and a pH value of 4.5. If the agent also contains invertase, the activity of the invertase per dose unit should be between 50 and 250,000 SU, preferably between 100 and 150,000 SU and particularly preferably between 150 and 100,000 SU per dose unit.

The activity of maltase is defined in units, wherein one unit is the amount of maltase which will convert maltose to D-glucose at a rate of one milligram per minute at 37° C. and a pH of 4.0 in a 10% maltose solution by weight.

Where the agent also contains maltase, the activity per dose unit should be between 100 and 100,000 units, preferably between 200 and 50,000 units and particularly preferably between 500 and 20,000 units.

In the case of hereditary fructose intolerance, it is particularly preferable if, in addition to glucose isomerase, folic acid in an amount of 1 mg to 100 mg, preferably 2 mg to 50 mg and particularly preferably 3 mg to 10 mg per dose unit are added to the agent(s) according to the present invention, as folic acid increases aldolase B activity.

It may also be advantageous to add metal ions to the agent according to the present invention, especially cations such as $Mn^{2+}$, $Mg^{2+}$, $Ca^{2+}$, $Zn^{2+}$, $Fe^{2+}$, $Co^{2+}$ or $Cu^{2+}$, including mixtures thereof, preferably at a molar ratio of $10^{-6}$ to $10^{-2}$. For the (xylose) glucose isomerase from Yamanaka described above, a particularly suitable cation is $Mn^{2+}$.

If the agent is added to a foodstuff before eating or during production, the activity of glucose isomerase should be between 0.01 and 20,000 units, preferably between 0.05 and 10,000 units and particularly preferably between 0.1 and 1,000 units per gram fructose in the foodstuff.

The capsule sizes mentioned below refer to the sizes defined by Capsugel Belgium BVBA, Bornem, Belgium. The size of capsules should be chosen in accordance with the specified formulation of the agent.

An agent in capsule form (e.g. of size 3) could contain, e.g., 15 mg glucose isomerase (activity of glucose isomerase 1 GIU/mg) and 135 mg dicalcium phosphate per capsule.

If capsules, e.g. of size 1, are used, they may contain 50 mg glucose isomerase (activity of glucose isomerase 1 GIU/mg), 5 mg folic acid and 150 mg maltodextrin per capsule.

A further example of a composition for the production of capsules consists of capsules of size 3 that contain 15 mg glucose isomerase (activity of glucose isomerase 1 GIU/mg), 75 mg 5-D-fructose dehydrogenase (activity of 5-D-fructose dehydrogenase 90 units/mg) and 60 mg dicalcium phosphate per capsule.

A further example of a composition for the production of capsules consists of capsules of size 00 that contain 300 mg glucose isomerase (activity of glucose isomerase 1 GIU/mg) and 170 mg dicalcium phosphate per capsule.

A unit dosage form in accordance with embodiments of the invention may for example contain between 0.01 and 100,000 GIU (=glucose isomerase units) and between 1 mg and 100 mg folic acid per dose unit. In addition, suitable additives in the required amount may be used.

An agent in accordance with embodiments of the invention can be made available for medical purposes and non-medical purposes, e.g. as a pharmaceutical composition, medical device, foodstuff, foodstuff for particular nutritional uses, food for special medical purposes, medical food, food supplement, dietary supplement, dietetic food supplement, health food, nutraceutical, or food additive.

In accordance with embodiment of the invention, an agent can be used to considerably alleviate or eliminate the symptoms and health impairments caused by fructose intolerance. The invention presented here is suitable for use in the case of fructose intolerance and for the therapeutic treatment of fructose intolerance.

The invention claimed is:

1. A method of reducing in a subject at least one of (a) the bioavailability of fructose in the body of said subject, (b) the amount of fructose available to the body of said subject and (c) the amount of fructose available to intestinal bacteria colonizing in the intestine of said subject, the subject being a person who would benefit from such reducing, the method comprising administering to the subject an amount of a glucose isomerase sufficient to effect such reducing in said subject, wherein said glucose isomerase is not administered in combination with an effective amount of 5-D-fructose-dehydrogenase.

2. The method of claim 1, wherein said subject suffers from fructose intolerance.

3. The method of claim 2, wherein said subject suffers from intestinal fructose intolerance.

4. The method of claim 3, wherein said intestinal fructose intolerance is caused by a disorder of fructose absorption.

5. The method of claim 1, wherein the administration occurs after the intake by said subject of fructose or a substance or foodstuff containing fructose in pure form or from which fructose can be released in the digestive tract.

6. The method of claim 1, wherein said glucose isomerase is contained in a pharmaceutical composition or a foodstuff.

7. The method of claim 6, wherein said glucose isomerase is contained in a pharmaceutical composition.

8. The method of claim 6, wherein said glucose isomerase is contained in a foodstuff.

9. The method of claim 8, wherein the foodstuff is selected from the group consisting of (a) foodstuffs for particular nutritional uses; (b) foods for special medical purposes; (c) medical foods; (d) food supplements; (e) dietary supplements; (f) dietetic food supplements; (g) health foods; (h) nutraceuticals; and (i) food additives.

10. The method of claim 9, wherein the foodstuff is a dietary supplement.

11. The method of claim 1, wherein said glucose isomerase is administered orally.

12. The method of claim 11, wherein the glucose isomerase is administered prior to said subject's eating, concurrently with said subject's eating or after said subject's eating.

13. The method of claim 11, wherein the glucose isomerase is formulated in a form selected from the group consisting of (a) coated or non-coated capsules (b) coated or non-coated tablets (c) capsules containing coated or non-coated pellets, granules, or micro- or mini-tablets (d) tablets pressed from coated or non-coated pellets, dragees, or micro- or mini-tablets (e) gel caps (f) a solution, (g) drops, (h) a suspension (i) a gel and (j) a powder.

14. The method of claim 13, wherein the coating of the capsules, tablets, pellets, granules, micro- or mini-tablets and dragees is selected from the group consisting of cellulose acetate phthalate, cellulose derivatives, shellac, polyvinylpyrrolidone derivatives, acrylic acid, polyacrylic acid derivatives and polymethyl methacrylate.

15. The method of claim 1, wherein said glucose isomerase is administered with at least one metal ion.

16. The method of claim 15, wherein the metal ion is selected from the group consisting of $Mn^{2+}$, $Mg^{2+}$, $Ca^{2+}$, $Zn^{2+}$, $Fe^{2+}$, $Co^{2+}$, $Cu^{2+}$ and mixtures thereof.

17. The method of claim 1, wherein the glucose isomerase is a xylose isomerase.

18. The method of claim 1, wherein said glucose isomerase is administered with a second enzyme which cleaves fructose from a sugar which is more complex than fructose.

19. The method of claim 18, wherein said second enzyme is selected from the group consisting of invertase, maltase and combinations thereof.

* * * * *